United States Patent
Terskikh et al.

(10) Patent No.: US 9,157,061 B2
(45) Date of Patent: Oct. 13, 2015

(54) METHODS FOR CULTURE AND PRODUCTION OF SINGLE CELL POPULATIONS OF HUMAN EMBRYONIC STEM CELLS

(75) Inventors: Alexey Terskikh, San Diego, CA (US); Ruchi Bajpai, Redwood City, CA (US)

(73) Assignee: BURNHAM INSTITUTE FOR MEDICAL RESEARCH, San Diego, CA (US)

( * ) Notice: Subject to any disclaimer, the term of this patent is extended or adjusted under 35 U.S.C. 154(b) by 0 days.

(21) Appl. No.: 13/164,639

(22) Filed: Jun. 20, 2011

(65) Prior Publication Data
US 2012/0034618 A1     Feb. 9, 2012

Related U.S. Application Data (62) Division of application No. 11/807,223, filed on May 24, 2007, now Pat. No. 7,964,402.

(60) Provisional application No. 60/808,692, filed on May 25, 2006.

(51) Int. Cl.
| | |
|---|---|
| G01N 21/64 | (2006.01) |
| C12N 5/0735 | (2010.01) |
| C12Q 1/02 | (2006.01) |

(52) U.S. Cl.
CPC .......... *C12N 5/0606* (2013.01); *C12N 2509/00* (2013.01)

(58) Field of Classification Search
CPC .......................... C12N 2509/00; C12N 5/0606
See application file for complete search history.

(56) References Cited

U.S. PATENT DOCUMENTS

| | | | |
|---|---|---|---|
| 5,675,063 | A | 10/1997 | Knight |
| 5,690,926 | A | 11/1997 | Hogan |
| 6,090,622 | A | 7/2000 | Gearhart et al. |
| 7,217,569 | B2 | 5/2007 | Thomson |
| 8,008,075 | B2 | 8/2011 | Green et al. |
| 8,153,429 | B2 | 4/2012 | Robins et al. |
| 2003/0017589 | A1* | 1/2003 | Mandalam et al. ........... 435/366 |
| 2004/0014210 | A1 | 1/2004 | Jessell et al. |

FOREIGN PATENT DOCUMENTS

| | | |
|---|---|---|
| WO | 9622362 | 7/1996 |
| WO | WO 2006020919 A2 * | 2/2006 |
| WO | 2006002674 | 3/2006 |

OTHER PUBLICATIONS

StemPro Accutase Cell Dissociation Reagent, accessed at http://www.lifetechnologies.com/us/en/home/life-science/stem-cell-research/stem-cell-culture/stem-cell-research-misc/stempro-accutase.html, pp. 1-3 on Nov. 26, 2014.*

"Accutase" accessed from http://www.accutase.com/accutase.html on Nov. 26, 2014, pp. 1-2.*
Reubinoff et al. 2000, Nature Biotechnology, vol. 18, pp. 399-404.*
Reijo et al. 2009, Differentiation, vol. 78, pp. 18-23.*
"Accutase", www.innovativecelltech.com, 2008, 1-11.
Amit, et al. "Clonally Derived Human Embryonic Stem Cell Lines Maintain Pluripotency and Proliferative Potential for Prolonged Periods of Culture", Developmental Biology 227, 2000, 271-278.
Amit, et al,, "Feeder Layer- and Serum-Free Culture of Human Embryonic Stem Cells". Biol. Reproduction 70, 2004, 837-845.
Beattie, et al., "Activin A Maintains Pluripotency of Human Embryonic Stem Cells in the Absence of Feeder Cells", Stem Cells 23, 2005, 489-96, Abstract.
Bongso, et al., "Isolation and culture of inner cell mass cells from human blastocysts", Hum Reprod. 9, 1994, 2110-2117.
Buzzard, et al., "Karyotype of human ES cells during extended culture.", Nat Biotechnol 22, 2004, 381-2.
Conti, et al,, "Niche-Independent Symmetrical Self-Renewal of a Mammalian Tissue Stem Cell", PLoS Biol 3:, 2005, e283.
Cowan, et al., "Derivation of embryonic stem-cell lines from human blastocysts.", New England Journal of Medicine. 350, 2004, 1353-6.
Dabeva, et al., "Activation, proliferation, and differentiation of progenitor cells into hepatocytes in the D-galactosamine model of liver regeneration", Am J Pathol 143, 1993, 1606-20.
Doetschman, et al., "The in vitro development of blastocyst-derived embryonic stem cell lines: formation of visceral yolk sac, blood islands and myocardium.", J Embryol Exp Morphol 87, 1985, 27-45.
Durcova. et al., "Immunomagnetic Isolation of Mouse Embryonic Stem Cells from Heterogeneous Cell Population", Journal of Reproduction and Development, vol. 44, No. 1, 1998, 85-89.
Ellerström, et al., "Facilitated expansion of human embryonic stem cells by single-cell enzymatic dissociation", Stem Cells 25, 2007, 1690-6.
Fuhrmann, et al., "Repression of Oct-4 during embryonic cell differentiation correlates with the appearance of TRIF, a transiently induced DNA-binding factor", Cell Mol Biol 45, 1999, 717-24.
Furusawa, et al, "Embryonic Stem Cells Expressing Both Platelet Endothelial Cell Adhesion Molecule-1 and Stage-Specific Embryonic Antigen-1 Differentiate Predominantly into Epiblast Cells in a Chimeric Embryo", Biology of Reproduction 70, 2004, 1452-1457.
Gardner, et al., "Culture and transfer of human blastocysts increases implantation rates and reduces the need for multiple embryo transfers", Fertil Steril 69, 1998, 84-8.
Gerrard, et al., "Stably transfected human embryonic stem cell clones express OCT4-specific green fluorescent protein and maintain self-renewal and pluripotency", Stem Cells 23, 2005, 124-33.

(Continued)

*Primary Examiner* — Thaian N Ton
(74) *Attorney, Agent, or Firm* — The Law Office of Jane K. Babin, Professional Corporation; Jane K. Babin (57) ABSTRACT

We used ACCUTASE®, a commercially available cell detachment solution, for single cell propagation of pluripotent hESCs. Unlike trypsin dissociation, ACCUTASE® treatment does not significantly affect the plating efficiency of hESC dissociation into single cells. Cultures dissociated with ACCUTASE® to single cells at each passage maintain a higher proportion of pluripotent cells as compared to collagenase-passaged hESCs. ACCUTASE®-treated hESCs can be grown to a high density as monolayers, and yet retain their pluripotency.

7 Claims, 4 Drawing Sheets

(56) References Cited

OTHER PUBLICATIONS

Hasegawa, et al., "A method for the selection of human embryonic stem cell sublines with high replating efficiency after single-cell dissociation", Stem Cells 24, 2006, 2649-60.

Heng, et al., "Mechanical dissociation of human embryonic stem cell colonies by manual scraping after collagenase treatment is much more detrimental to cellular viability than is trypsinization with gentle pipetting", Biotechnol Appl Biochem. 47(Pt 1), 2007, 33-7.

Joannides, et al., "Automated mechanical passaging: a novel and efficient method for human embryonic stem cell expansion", Stem Cells 24, 2006, 230-5.

Kim, et al., "Dopamine neurons derived from embryonic stem cells function in an animal model of Parkinson's disease", Nature 418, 2002, 50-6.

Klimanskaya, et al., "Human embryonic stem cells derived without feeder cells", Lancet 365, 2005, 1636-41.

Li, , "Cardiomyocyte transplantation improves heart function", Ann Thorac Surg 62, 1996, 654-60.

Maitra, et al., "Genomic alterations in cultured human embryonic stem cells", Nat Genet 37, 2005, 1099-103.

McDonald, et al., "Transplanted embryonic stem cells survive, differentiate and promote recovery in injured rat spinal cord", Nat Med 5, 1999, 1410-2.

Min, et al., "Transplantation of embryonic stem cells improves cardiac function in postinfarcted rats", J Appl Physiol 92, 2002, 288-96.

Mitalipova, et al., "Preserving the genetic integrity of human embryonic stem cells.", Nat Biotechnol. 23, 2005, 19-20.

Ovitt, et al., "The molecular biology of Oct-4 in the early mouse embryo.", Mol Hum Reprod 4, 1998, 1021-31.

Sakai, et al., "Autologous heart cell transplantation improves cardiac function after myocardial injury", Ann Thorac Surg. Dec. 1999;68, 1999, 2074-80.

Scholer, et al., "Oct-4: a germline-specific transcription factor mapping to the mouse t-complex.", EMBO J. 9, 1990, 2185-95.

Sidhu, et al., "Derivation of Three Clones from Human Embryonic Stem Cell Lines by FACS Sorting and Their Characterization", Stem Cells and Development 15, 2006, 61-69.

Sperger, et al., "Gene expression patterns in human embryonic stem cells and human pluripotent germ cell tumors.", Proc Nati Acad Sci U S A. 100, 2003, 13350-5.

Stojkovic, "Human-Serum Matrix Supports Undifferentiated Growth of Human Embryonic Stem Cells", Stem Cells 23, 2005, 895-902.

Takakura, et al., "PDGFR alpha expression during mouse embryogenesis: immunolocalization analyzed by whole-mount immunohistostaining using the monoclonal anti-mouse PDGFR alpha antibody APA5", J Histochem Cytochem 45, 1997, 883-93.

Thomson, et al., "Embryonic stem cell lines derived from human blastocysts", Science. 282, 1998, 1145-7.

Thomson, et al., "Isolation of a primate embryonic stem cell line", PNAS 92, 1995, 7844-784.

Wachs, et al., "High efficacy of clonal growth and expansion of adult neural stem cells", Lab invest 83, 2003, 949-62.

Watanabe, et al., "Cardiomyocyte transplantation in a porcine myocardial infarction model", Cell Transplant 7, 1998, 239-46.

"Basic FGF and suppression of BMP signaling sustain undifferentiated proliferation of human ES cells", Nat Methods 2, 2005, 185-90.

Xu, et al., "Feeder Free Growth of Undifferentiated Human Embryonic Stem Cells", Nature Biotech. 19, 2001, 971-974.

Yeom, et al., "Germline regulatory element of Oct-4 specific for the totipotent cycle of embryonal cell", Development 122, 1996, 881-94.

* cited by examiner

METHODS FOR CULTURE AND PRODUCTION OF SINGLE CELL POPULATIONS OF HUMAN EMBRYONIC STEM CELLS

CROSS-REFERENCE TO RELATED APPLICATIONS

This application is a divisional of Ser. No. 11/807,223, filed May 24, 2007, now U.S. Pat. No. 7,964,402, issued on Jun. 21, 2011, which in turn claims priority from U.S. Provisional Application Ser. No. 60/808,692 filed May 25, 2006, which is incorporated herein by reference.

STATEMENT OF GOVERNMENT RIGHTS

The invention was supported, at least in part, by a grant from the Government of the United States of America (grant no. HD047313 from the National Institutes of Health). The Government may have certain rights to the invention.

BACKGROUND OF THE INVENTION

A significant amount of the space between the cells in the monolayer is occupied by a complex network of proteins and polysaccharides which is referred to as an extracellular matrix (ECM). The ECM consists of two subgroups of molecules: extracellular matrix molecules (ECM molecules) and cell adhesion molecules (CAMs). ECM molecules include collagen, proteoglycans and non-collagen glycoproteins, and CAMs are comprised of the immunoglobulin superfamily of CAMs (IgCAMs), cadherins, selectins, and integrins. The function of the ECM molecules were thought to have been purely structural due to their large presence in connective tissue, but the ECM appears to play a role in survival, development, migration, proliferation and function of the cells immediately surrounding it.

To maintain proliferating cells in culture for an extended period of time, it is necessary to subculture the cells (remove them from one culture vessel, and place them in a new culture vessel containing fresh medium and a lower cell concentration). Each time a population of cells is subcultured, it is referred to as a passage. In order to move the cells from the first culture vessel to the second culture vessel, the monolayer of cells have to be detached from the surface of the first culture vessel, and then dissociated into a single cell suspension. Then, the single cell suspension can be transferred to the fresh culture vessel. Single cells are necessary for basic biological research. For example, cell sorting methods are used to determine the composition of heterogeneous cell populations, and to isolate specific subpopulations of cells with desirable characteristics which can then be used to conduct further research, or used therapeutically in a clinical setting. Cell sorting methods can only be used effectively on single cells. The generation of a single cell suspension also has applications in other areas such as the production of biomolecules and clinical diagnostics.

In addition to isolating cells from primary tissues and subculturing cells in existing cultures, the generation of single cell suspensions is extremely important for a variety of applications. For example, during cell therapy, single cells are delivered to certain sites in order to treat specific conditions. Transplanting aggregates is undesirable because (i) aggregates can plug the delivery device (ii) it is difficult to estimate the number of actual cells that are delivered (iii) cells in aggregates are more susceptible to cell death due to the nutrient and oxygen mass transfer limitations that they suffer and (iv) aggregates are less likely to migrate to areas of damage, respond to local cues, and integrate into the host cellular architecture. Single cells are also necessary for basic biological research. For example, cell sorting methods are used to determine the composition of heterogeneous cell populations, and to isolate specific subpopulations of cells with desirable characteristics which can then be used to conduct further research, or used therapeutically in a clinical setting. Cell sorting methods can only be used effectively on single cells. The generation of a single cell suspension also has applications in other areas such as the production of biomolecules and clinical diagnostics.

Several methods have been developed to generate single cell suspensions from primary tissues, attached cells in culture, and aggregates in culture. These methods involve the use of physical forces (mechanical dissociation), enzymes (enzymatic dissociation), or a combination of both. Mechanical means of detaching cells that are attached to a surface include the use of cell scrapers. Mechanical means of separating cells which are attached to one another include trituration through a narrow bore pipette, fine needle aspiration, vortex disaggregation, and forced filtration through a fine nylon or stainless steel mesh. Whereas all of these methods are effective in creating single cell suspensions, the excessive physical forces involved often result in a significant amount of cell death and cell damage. In situations where the generation of a suspension of viable single cells is the ultimate goal, cell death and cell damage are extremely undesirable. Moreover the manual nature of certain mechanical dissociation protocols (e.g., trituration, which is done by hand) often make it difficult compare measured values (such as cell viability) from different sources since dissociation efficiency varies between individuals. In fact, the manual nature of this procedure may contribute to differences in the physical attributes (e.g., cell concentration, cell viability, cell size distribution etc.) between two otherwise identical samples.

In an attempt to avoid the negative consequences of mechanical dissociation, researchers have used enzymes (either alone or in combination) which are directed towards one or more components in the ECM, also known as passage enzymes. Certain enzymes are known to target and cleave specific molecules present within the ECM. For example, the enzyme trypsin (which cleaves polypeptide chains on the carboxyl side of arginine and lysine residues) is commonly used to detach and dissociate monolayer cultures, whereas collagenase is often used to dissociate primary tissues and aggregates. However, not all cell types can be easily dissociated using enzymes. For those cell types that are susceptible to enzymatic dissociation, it has been shown that enzymes can be detrimental to the cells and negatively impact the ability of the generated single cells to subsequently survive and or divide. For example, when neural stem cell (NSC) aggregates were dissociated using trypsin, the growth rate of the single cells in subsequent culture was found to have been adversely affected relative to single cells generated using mechanical dissociation. This result may be attributable to the fact that trypsin is known to cleave certain classes of cell surface transmitter receptors. In the extreme, enzymes can completely destroy cells. For example, collagenase has been shown to reduce viable cells to debris when used to dissociate neural stem cell aggregates.

Embryonic stem cells (ESCs) are primitive, undifferentiated cells obtained from the inner cell mass of blastocysts prior to the implantation stage in the mammalian uterine endometrium. These undifferentiated cells are deemed pluripotent since they have the ability to differentiate and yield many types of cells. For ESCs to remain undifferentiated in vitro, they need to attach to a substrate, or else the cells aggregate in suspension to form embryoid bodies and start to differentiate. The culture used to grow ESCs provides a surface for the cells to attach. Currently hESCs are propagated as clusters. These clusters need to be manually cleaned and selected with every passage. Due to the difficulty in manipulating the cell clusters, the clusters are exposed to dislodging enzymes, such as trypsin or collagenase, after the initial passages performed via mechanical dissociation. These enzymes significantly increase the level of cell death.

Human embryonic neural stem cells inoculated into serum free medium can be induced to divide and form aggregates over time. Visually, the aggregates contain a significantly greater amount of extracellular matrix compared to embryonic neural stem cell aggregates derived from mice. Currently, the state-of-the-art method of generating a single cell suspension from these aggregates involves mechanical dissociation. However, due to the large quantities of extracellular matrix, mechanical dissociation of human neurosphere aggregates results in a much greater cell death relative to that caused during the mechanical dissociation of murine neural stem cell aggregates. Even in the hands of an experienced researcher, it is not unusual to obtain measured cell viabilities of 50% or less.

Pancreatic stem cells are cells that are believed to give rise to all of the different endocrine tissues within the pancreas. It is anticipated that research efforts that are presently underway using these cells will eventually lead to cell therapy aimed at eliminating Type I diabetes, a currently incurable disease afflicting millions of individuals. At present, due to the prevalence of this disease, and the associated economic impact, there is an extensive amount of research being conducted in an effort to expand this stem cell population. Pancreatic stem cells are obtained from whole pancreatic tissue through a series of fractionations. The fraction containing the stem cells is isolated from the other fractions and placed into a serum free medium. Currently, there are no methods available to expand these cells in vitro. Rather, the medium simply serves to maintain the cells in culture, and delay cell death. The cells in this fraction, including the stem cells are present as large aggregates of primary tissue. Large aggregates are undesirable since cells rapidly begin to die due to nutrient and oxygen limitations. Thus, in order to ensure that the cells survive, and to isolate the stem cells from the rest of the cells, it is necessary to dissociate the tissue into a single cell suspension. At present, there are no reliable or reproducible methods to accomplish this. Until now, the best method utilized by researchers, and the current accepted practice in this field has been to mechanically dissociate the aggregates. However, this method does not result in the generation of a single cell suspension. Rather, many cell aggregates remain. Significantly increasing the intensity and duration of the mechanical dissociation process does not remove these aggregates, but rather, results in the death of large numbers of otherwise viable cells. Thus, despite being the most commonly used procedure in this field, mechanical dissociation is not ideal.

In light of the problems with prior art methods of creating single cell suspensions of viable pluripotent hESCs, a need exists for a new approach that increases the efficiency and ease of culturing hESCs and reduces the negative results of mechanical and enzymatic dissociation.

SUMMARY OF THE INVENTION

The present invention is directed to methods of producing, culturing, and passaging viable, pluripotent embryonic stem cells (ESCs) and related methods and compositions.

According to one embodiment of the invention, a method is provided for preparing embryonic stem cells comprising (a) providing a colony of embryonic stem cells and (b) enzymatically dissociating the colony of embryonic stem cells to produce a plurality of single embryonic stem cells, wherein greater than 75, 80, 85 or 90 percent of said plurality of single embryonic stem cells are viable and pluripotent. The embryonic stem cells treated by this method may be any embryonic stem cells, including, but not limited to human or other primate stem cells. The term "colony" is meant herein to include colonies of embryonic stem cells, as the term is commonly understood in the art of cell culture, monolayers of cells growing in a culture vessel, and other such cell layers or aggregates resulting from growth of single embryonic stem cells in culture.

According to another embodiment, a substantially greater proportion of the population of single embryonic stem cells produced by this method are undifferentiated than an otherwise similar population of single embryonic stem cells produced by collagenase digestion of a colony of embryonic stem cells, for example. According to another embodiment, the single embryonic stem cells produced by this method are karyotypically similar to said colony of embryonic stem cells; that is, the process of producing single embryonic stem cells does not cause the sort of gross genetic abnormalities that often result from the use of trypsin to dissociate stem cell colonies or monolayers. According to another embodiment, the method comprises flow-sorting said plurality of single embryonic stem cells. According to another embodiment, the method comprises depositing at least one of the single embryonic stem cells into a well of a multi-well plate. For example, according to one embodiment, the method comprises flow-sorting said plurality of single embryonic stem cells to provide a flow-sorted embryonic stem cell and depositing the flow-sorted embryonic stem cells into a well of a multi-well plate. According to another embodiment the method further comprises growing a plurality of colonies of embryonic stem cells from the plurality of single embryonic stem cells. Embryonic stem cell colonies produced by the methods of the invention have a substantially uniformly undifferentiated colony morphology.

According to another embodiment of the invention, methods are provided for preparing embryonic stem cells comprising (a) providing a colony of embryonic stem cells and (b) non-mechanically dissociating the colony of embryonic stem cells to produce a plurality of single embryonic stem cells, wherein greater than 75 percent of said plurality of single embryonic stem cells are viable and pluripotent.

According to another embodiment of the invention, methods are provided for passaging embryonic stem cells comprising (a) providing a colony of embryonic stem cells in a first culture vessel; (b) dissociating the colony of embryonic stem cells enzymatically to produce a plurality of single embryonic stem cells, wherein greater than 75 percent of said plurality of single embryonic stem cells are viable and pluripotent; (c) transferring one or more of said single embryonic stem cells to a second culture vessel; and (d) growing a colony of embryonic stem cells from said one or more single embryonic stem cell in the second culture vessel. The culture vessels may be any vessel used for mammalian cell culture, such as, for example, wells of a multi-well plate. Steps (b) through (d) may be repeated for serially passaging the cells. According to another embodiment, the monolayer in the first culture vessel is dissociated to produce said plurality of single embryonic stem cells without mechanical dissociation. According to another embodiment, the method comprises flow sorting the plurality of single embryonic stem cells. For example, in association with flow sorting, such a method may comprise identifying a single embryonic stem cell having a desired phenotype and depositing the single embryonic stem cell having the desired phenotype in a second culture vessel.

According to another embodiment of the invention, methods are provided for passaging embryonic stem cells comprising (a) providing a colony of embryonic stem cells; (b) non-mechanically dissociating the colony of embryonic stem cells to produce a plurality of single embryonic stem cells, wherein greater than 75 percent of said plurality of single embryonic stem cells are viable and pluripotent; (c) flow-sorting the plurality of single embryonic stem cells, (d) depositing one or more single flow-sorted embryonic stem cells into a second culture vessel; and (e) culturing said one or more single flow-sorted embryonic stem cells to produce a colony of embryonic stem cells in the second culture vessel. Step (b) may, for example, comprise enzymatically dissociating the colony of embryonic stem cells to produce the plurality of single embryonic stem cells.

According to another embodiment of the invention, methods are provided for screening embryonic stem cells comprising (a) providing a colony of embryonic stem cells; (b) dissociating the colony of embryonic stem cells enzymatically to produce a plurality of single embryonic stem cells, wherein greater than 75 percent of said plurality of single embryonic stem cells are viable and pluripotent; (c) flow-sorting said plurality of single embryonic stem cells to produce flow-sorted embryonic stem cells; (d) depositing one or more of said flow-sorted embryonic stem cells into a well of a multi-well plate; and (e) introducing a substance into the well of the multi-well plate; and (f) observing a phenotype of said one or more flow-sorted embryonic stem cells in the well in response to the introduction of the substance.

Any of the aforementioned methods may be automated.

According to another embodiment of the invention, compositions are provided that comprise a plurality of single embryonic stem cells produced by enzymatic dissociation of a colony of embryonic stem cells, wherein greater than 75, 80, 85 or 90 percent of said population of single embryonic stem cells are viable and pluripotent. According to another embodiment, substantially greater proportion of said plurality of single embryonic stem cells are undifferentiated than an otherwise similar population of single embryonic stem cells produced by collagenase digestion of a colony of embryonic stem cells. According to another embodiment, the plurality of single embryonic stem cells are karyotypically similar to the colony of embryonic stem cells.

The foregoing and other aspects of the invention will become more apparent from the following detailed description, accompanying drawings, and the claims.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below.

DETAILED DESCRIPTION OF THE INVENTION

Stem cells are cells capable of differentiation into other cell types, including those having a particular, specialized function (i.e., terminally differentiated cells, such as erythrocytes, macrophages, etc.), progenitor (i.e., "multipotent") cells which can give rise to any one of several different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming they are unable to de-differentiate into the cells from which they were derived. "Multipotent" stem/progenitor cells (e.g., neural stem cells) have a more narrow differentiation potential than do pluripotent stem cells. Another class of cells even more primitive (i.e., uncommitted to a particular differentiation fate) than pluripotent stem cells are the so-called "totipotent" stem cells (e.g., fertilized oocytes, cells of embryos at the two and four cell stages of development), which have the ability to differentiate into any type of cell of the particular species. For example, a single totipotent stem cell could give rise to a complete animal, as well as to any of the myriad of cell types found in the particular species (e.g., humans). In this specification, pluripotent and totipotent cells, as well as cells with the potential for differentiation into a complete organ or tissue, are referred as "primordial" stem cells.

Primordial stem cells promise to provide a supply of readily available cells and tissues of all types for use in transplantation, cell regeneration and replacement therapy, drug discovery, generation of model systems for studying mammalian development, and gene therapy.

DEFINITIONS

"Basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves can not synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that can be supplemented with bFGF, insulin, and ascorbic acid and which supports the growth of primate primordial stem cells in a substantially undifferentiated state can be employed.

"Conditioned medium" refers to a growth medium that is further supplemented with soluble factors derived from cells cultured in the medium. Techniques for isolating conditioned medium from a cell culture are well known in the art. As will be appreciated, conditioned medium is preferably essentially cell-free. In this context, "essentially cell-free" refers to a conditioned medium that contains fewer than about 10%, preferably fewer than about 5%, 1%, 0.1%, 0.01%, 0.001%, and 0.0001% than the number of cells per unit volume, as compared to the culture from which it was separated.

A "defined" medium refers to a biochemically defined formulation comprised solely of the biochemically-defined constituents. A defined medium may include solely constituents having known chemical compositions. A defined medium may also include constituents that are derived from known sources. For example, a defined medium may also include factors and other compositions secreted from known tissues or cells; however, the defined medium will not include the conditioned medium from a culture of such cells. Thus, a "defined medium" may, if indicated, include one or more particular compounds added to form the culture medium, up to and including a portion of a conditioned medium that has been fractionated to remove at least one component detectable in a sample of the conditioned medium that has not been fractionated. Here, to "substantially remove" of one or more detectable components of a conditioned medium refers to the removal of at least an amount of the detectable, known component(s) from the conditioned medium so as to result in a fractionated conditioned medium that differs from an unfractionated conditioned medium in its ability to support the long-term substantially undifferentiated culture of primate stem cells. Fractionation of a conditioned medium can be performed by any method (or combination of methods) suitable to remove the detectable component(s), for example, gel filtration chromatography, affinity chromatography, immune precipitation, etc. Similarly, or a "defined medium" may include serum components derived from an animal, including human serum components. In this context, "known" refers to the knowledge of one of ordinary skill in the art with reference to the chemical composition or constituent.

A "dissociation solution" is a solution comprising at least one proteolytic enzyme and at least one collagenolytic enzyme that is useful for the detachment and dissociation of anchorage-dependent cells such as human embryonic stem cells (hESCs). Preferably, the enzymes are in an aqueous solution that is physiologically compatible, e.g., suitable for the culture of hESCs. A preferred dissociation solution is Accutase™ (Innovative Cell Technologies, Inc., San Diego, Calif.), a mixture of proteolytic and collagenolytic enzymes extracted from an invertebrate species in Dulbecco's PBS (0.2 g/l KCl, 0.2 g/l $KH_2PO_4$, 8 g/l NaCl, 1.15 g/l $Na_2HPO_4$) containing 0.5 mM EDTA.4Na and 3 mg/ml Phenol Red.

"A mixture of enzymes with proteolytic, collagenolytic and DNAse activities" has special meaning in this application such that it specifically refers only to ACCUTASE® a commercial solution readily available from several manufacturers (e.g., Innovative Cell Technologies, Chimicon/Millipore).

"Embryonic germ cells" or "EG cells" are cells derived from the primordial germ cells of an embryo or fetus that are destined to give rise to sperm or eggs. EG cells are among the embryonic stem cells that can be cultured in accordance with the invention.

"Embryonic stem cells" or "ES cells" are cells obtained from an animal (e.g., a primate, such as a human) embryo, preferably from an embryo that is less than about eight weeks old. Preferred embryonic stages for isolating primordial embryonic stem cells include the morula or blastocyst stage of a pre-implantation stage embryo.

"Extracellular matrix" or "matrix" refers to one or more substances that provide substantially the same conditions for supporting cell growth as provided by an extracellular matrix synthesized by feeder cells. The matrix may be provided on a substrate. Alternatively, the component(s) comprising the matrix may be provided in solution.

"Feeder cells" are non-primordial stem cells on which stem cells, particularly primate primordial stem cells, may be plated and which provide a milieu conducive to the growth of the stem cells.

A cell culture is "essentially feeder-free" when it does not contain exogenously added conditioned medium taken from a culture of feeder cells nor exogenously added feeder cells in the culture, where "no exogenously added feeder cells" means that cells to develop a feeder cell layer have not been purposely introduced for that reason. Of course, if the cells to be cultured are derived from a seed culture that contained feeder cells, the incidental co-isolation and subsequent introduction into another culture of some small proportion of those feeder cells along with the desired cells (e.g., undifferentiated primate primordial stem cells) should not be deemed as an intentional introduction of feeder cells. Similarly, feeder cells or feeder-like cells that develop from stem cells seeded into the culture shall not be deemed to have been purposely introduced into the culture.

A "growth environment" is an environment in which stem cells (e.g., primate primordial stem cells) will proliferate in vitro. Features of the environment include the medium in which the cells are cultured, and a supporting structure (such as a substrate on a solid surface) if present.

"Growth factor" refers to a substance that is effective to promote the growth of stem cells and which, unless added to the culture medium as a supplement, is not otherwise a component of the basal medium. Put another way, a growth factor is a molecule that is not secreted by cells being cultured (including any feeder cells, if present) or, if secreted by cells in the culture medium, is not secreted in an amount sufficient to achieve the result obtained by adding the growth factor exogenously. Growth factors include, but are not limited to, basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, and bone morphogenic proteins (BMPs), insulin, cytokines, chemokines, morphogents, neutralizing antibodies, other proteins, and small molecules.

"Isotonic" refers to a solution having essentially the same tonicity (i.e., effective osmotic pressure equivalent) as another solution with which it is compared. In the context of cell culture, an "isotonic" medium is one in which cells can be cultured without an appreciable net flow of water across the cell membranes.

A solution having "low osmotic pressure" refers to a solution having an osmotic pressure of less than about 300 milliosmols per kilogram ("mOsm/kg").

A "non-essential amino acid" refers to an amino acid species that need not be added to a culture medium for a given cell type, typically because the cell synthesizes, or is capable of synthesizing, the particular amino acid species. While differing from species to species, non-essential amino acids are known to include L-alanine, L-asparagine, L-aspartic acid, L-glutamic acid, glycine, L-proline, and L-serine.

A "primate-derived primordial stem cell" or "primate primordial stem cell" is a primordial stem cell obtained from a primate species, including humans and monkeys, and includes genetically modified primordial stem cells.

"Pluripotent" refers to cells that are capable of differentiating into one of a plurality of different cell types, although not necessarily all cell types. An exemplary class of pluripotent cells is embryonic stem cells, which are capable of differentiating into any cell type in the human body. Thus, it will be recognized that while pluripotent cells can differentiate into multipotent cells and other more differentiated cell types, the process of reverse differentiation (i.e., de-differentiation) is likely more complicated and requires "re-programming" the cell to become more primitive, meaning that, after re-programming, it has the capacity to differentiate into more or different cell types than was possible prior to re-programming.

A cell culture is "essentially serum-free" when it does not contain exogenously added serum, where no "exogenously added feeder cells" means that serum has not been purposely introduced into the medium. Of course, if the cells being cultured produce some or all of the components of serum, of if the cells to be cultured are derived from a seed culture grown in a medium that contained serum, the incidental co-isolation and subsequent introduction into another culture of some small amount of serum (e.g., less than about 1%) should not be deemed as an intentional introduction of serum.

"Substantially undifferentiated" means that population of stem cells (e.g., primate primordial stem cells) contains at least about 50%, preferably at least about 60%, 70%, or 80%, and even more preferably, at least about 90%, undifferentiated, stem cells. Fluorescence-activated cell sorting using labeled antibodies or reporter genes/proteins (e.g., enhanced green fluorescence protein [EGFP]) to one or more markers indicative of a desired undifferentiated state (e.g., a primordial state) can be used to determine how many cells of a given stem cell population are undifferentiated. For purposes of making this assessment, one or more of cell surface markers correlated with an undifferentiated state (e.g., Oct-4, SSEA-4, Tra-1-60, and Tra-1-81) can be detected. Telomerase reverse transcriptase (TERT) activity and alkaline phosphatase can also be assayed. In the context of primate primordial stem cells, positive and/or negative selection can be used to detect, for example, by immunostaining or employing a reporter gene (e.g., EGFP), the expression (or lack thereof) of certain markers (e.g., Oct-4, SSEA4, Tra-1-60, Tra-1-81, SSEA-1, SSEA-3, nestin, telomerase, Myc, p300, and Tip60 histone acetyltransferases, and alkaline phosphatase activity) or the presence of certain post-translational modifications (e.g., acetylated histones), thereby facilitating assessment of the state of self-renewal or differentiation of the cells.

"Totipotent" refers to cells that are capable of differentiating into any cell type, including pluripotent, multipotent, and fully differentiated cells (i.e., cells no longer capable of differentiation into various cell types), such as, without limitation, embryonic stem cells, neural stem cells, bone marrow stem cells, hematopoietic stem cells, cardiomyocytes, neuron, astrocytes, muscle cells, and connective tissue cells.

Culturing Primate Stem Cells in a Substantially Undifferentiated State

Stem cells can be cultured by any known method and using any media used for culturing stem cells. For example, a defined, isotonic cell culture media can be used to culture stem cells, including primate primordial stem cells, particularly human embryonic stem cells, in a substantially undifferentiated state (see, e.g., U.S. Patent Application 60/435991). Such media may be essentially serum-free, and may not require the use of a feeder cell layer or conditioned medium from separate cultures of feeder cells, although one may initially culture the stem cells in a growth environment that includes allogeneic feeder cells (or conditioned medium from such cells) prior to transferring the cells to fresh, feeder-free cultures for serial passaging (e.g., 1-50 or more passages).

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other texts useful include Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Invitrogen, Nalgene-Nunc International, Sigma Chemical Co., Chemicon International, and ICN Biomedicals.

Primate-Derived Primordial Stem Cells

Stem cells, including primate primordial stem cells can be obtained from any suitable source using any appropriate technique. For example, procedures for isolating and growing human primordial stem cells are described in U.S. Pat. No. 6,090,622. Procedures for obtaining Rhesus monkey and other non-human primate primordial stem cells are described in U.S. Pat. No. 5,843,78 and international patent publication WO 96/22362. In addition, methods for isolating Rhesus monkey primordial stem cells are described by Thomson, et al., Proc. Natl. Acad. Sci. USA 92:7844-7848, 1995).

Human embryonic stem cells (hESCs) can be isolated, for example, from human blastocysts obtained from human in vivo preimplantation embryos, in vitro fertilized embryos, or one-cell human embryos expanded to the blastocyst stage (Bongso, et al., Hum. Reprod. 4:706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase (Sigma). The inner cell masses can be isolated by immunosurgery or by mechanical separation, and are plated on mouse embryonic feeder layers, or in the defined culture system as described herein. After nine to fifteen days, inner cell mass-derived outgrowths are dissociated into clumps either by exposure to calcium and magnesium-free phosphate-buffered saline (PBS) with 1 mM EDTA, by exposure to dispase, collagenase, or trypsin, or by mechanical dissociation with a micropipette. The dissociated cells are then replated as before in fresh medium and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about 200 U/mL), or by selection of individual colonies by mechanical dissociation, for example, using a micropipette.

Once isolated, the stem cells, e.g., primate stem cells, can be cultured in a culture medium according to the invention that supports the substantially undifferentiated growth of primate primordial stem cells using any suitable cell culturing technique. For example, a matrix laid down prior to lysis of primate feeder cells (preferably allogeneic feeder cells) or a synthetic or purified matrix can be prepared using standard methods. The primate primordial stem cells to be cultured are then added atop the matrix along with the culture medium. In other embodiments, once isolated, undifferentiated human embryonic stem cells can be directly added to an extracellular matrix that contains laminin or a growth-arrested human feeder cell layer (e.g., a human foreskin fibroblast cell layer) and maintained in a serum-free growth environment.

Alternatively, the stem cells, e.g., primate primordial stem cells, can be grown on living feeder cells (preferably allogeneic feeder cells) using methods known in the cell culture arts. The growth of the stem cells is then monitored to determine the degree to which they have become differentiated, for example, using a marker for alkaline phosphatase or telomerase or detecting the expression of the transcription factor Oct-4, or by detecting a cell surface marker indicative of an undifferentiated state (e.g., in the context of human embryonic stem cells, a labeled antibody for any one or more of SSEA-4, Tra-1-60, and Tra-1-81). When the culture has grown to confluence, at least a portion of the undifferentiated cells is passaged to another culture vessel. The determination to passage the cells and the techniques for accomplishing such passaging can be performed in accordance with the culture methods of invention (e.g., through morphology assessment and dissection procedures).

In certain embodiments, the cells are cultured in a culture vessel that contains a substrate selected from the group consisting of feeder cells, preferably allogeneic feeder cells, an extracellular matrix, a suitable surface and a mixture of factors that adequately activate the signal transduction pathways required for undifferentiated growth, and a solution-borne matrix sufficient to support growth of the stem cells in solution. Thus, in addition to the components of the solution phase of culture media of the invention, the growth environment includes a substrate selected from the group consisting of primate feeder cells, preferably allogeneic feeder cells, and an extracellular matrix, particularly laminin. Preferred feeder cells for primate primordial stem cells include primate fibroblasts and stromal cells. In other embodiments, the feeder cells and stem cells are allogeneic. In the context of human embryonic stem cells, particularly preferred feeder cells include human fibroblasts, human stromal cells, and fibroblast-like cells derived from human embryonic stem cells. If living feeder cells are used, as opposed to a synthetic or purified extracellular matrix or a matrix prepared from lysed cells, the cells can be mitotically inactivated (e.g., by irradiation or chemically) to prevent their further growth during the culturing of primate primordial stem cells. Inactivation is preferably performed before seeding the cells into the culture vessel to be used. The primate primordial stem cells can then be grown on the plate in addition to the feeder cells. Alternatively, the feeder cells can be first grown to confluence and then inactivated to prevent their further growth. If desired, the feeder cells may be stored frozen in liquid nitrogen or at −140° C. prior to use. As mentioned, if desired such a feeder cell layer can be lysed using any suitable technique prior to the addition of the stem cells (e.g., primate stem cells) so as to leave only an extracellular matrix.

Not wishing to be bound to any theory, it is believed that the use of such feeder cells, or an extracellular matrix derived from feeder cells, provides one or more substances necessary to promote the growth of stem cells (e.g., primate primordial stem cells) and/or prevent or decrease the rate of differentiation of such cells. Such substances are believed to include membrane-bound and/or soluble cell products that are secreted into the surrounding medium by the feeder cells. Thus, those skilled in the art will recognize that additional cell lines can be used with the cell culture media of the present invention to equivalent effect, and that such additional cell lines can be identified using standard methods and materials, for example, by culturing over time (e.g., several passages) substantially undifferentiated primate primordial stem cells on such feeder cells in a culture medium according to the invention and determining whether the stem cells remain substantially undifferentiated over the course of the analysis. Also, because of the defined nature of the culture media provided herein, it is now possible to assay various compounds found in the extracellular matrix or secreted by feeder cells to determine their respective roles in the growth, maintenance, and differentiation of stem calls such as primate primordial stem cells.

When purified components from extracellular matrices are used in lieu of feeder cells, such components will include those provided by the extracellular matrix of a suitable feeder cell layer. Components of extracellular matrices that can be used include laminin, or products that contain laminin, such as Matrigel™, or other molecules that activate the laminin receptor and/or its downstream signaling pathway. Matrigel™ is a soluble preparation from Engelbreth-Holm-Swarm tumor cells that gels at room temperature to form a reconstituted basement membrane. Other extracellular matrix components include fibronectin, collagen, and gelatin. In addition, one or more substances produced by the feeder cells, or contained in an extracellular matrix produced by a primate feeder cell line, can be identified and used to make a substrate that obviates the need for feeder cells. Alternatively, these components can be prepared in soluble form so as to allow the growth and maintenance of undifferentiated of stem cells in suspension culture. Thus, this invention contemplates adding extracellular matrix to the fluid phase of a culture at the time of passaging the cells or as part of a regular feeding, as well as preparing the substrate prior to addition of the fluid components of the culture.

Any suitable culture vessel can be adapted to culture stem cells (e.g., primate primordial stem cells) in accordance with the invention. For example, vessels having a substrate suitable for matrix attachment include tissue culture plates (including multi-well plates, pre-coated (e.g., gelatin-pre-coated) plates, T-flasks, roller bottles, gas permeable containers, and bioreactors. To increase efficiency and cell density, vessels (e.g., stirred tanks) that employ suspended particles (e.g., plastic beads or other microcarriers) that can serve as a substrate for attachment of feeder cells or an extracellular matrix can be employed. In other embodiments, undifferentiated stem cells can be cultured in suspension by providing the matrix components in soluble form. As will be appreciated, fresh medium can be introduced into any of these vessels by batch exchange (replacement of spent medium with fresh medium), fed-batch processes (i.e., fresh medium is added without removal of spent medium), or ongoing exchange in which a proportion of the medium is replaced with fresh medium on a continuous or periodic basis.

Differentiated Cells

Primate primordial stem cells (or other stem cells) can be used to prepare populations of differentiated cells of various commercially and therapeutically important tissue types. In general, this is accomplished by expanding the stem cells to the desired number. Thereafter, they are caused to differentiate according to any of a variety of differentiation strategies. For example, highly enriched populations of cells of the neural lineage can be generated by changing the cells to a culture medium containing one or more neurotrophins (such as neurotrophin 3 or brain-derived neurotrophic factor), one or more mitogens (such as epidermal growth factor, bFGF, PDGF, IGF 1, and erythropoietin), or one or more vitamins (such as retinoic acid, ascorbic acid). Alternatively, multipotent neural stem cells can be generated through the embryoid body stage and maintained in a chemically defined medium containing bFGF. Cultured cells are optionally separated based on whether they express a nerve precursor cell marker such as nestin, Musashi, vimentin, A2B5, nurr1, or NCAM. Using such methods, neural progenitor/stem cells can be obtained having the capacity to generate both neuronal cells (including mature neurons) and glial cells (including astrocytes and oligodendrocytes). Alternatively, replicative neuronal precursors can be obtained that have the capacity to form differentiated cell populations.

Cells highly enriched for markers of the hepatocyte lineage can be differentiated from primate primordial stem cells by culturing the stem cells in the presence of a histone deacetylase inhibitor such as n-butyrate. The cultured cells are optionally cultured simultaneously or sequentially with a hepatocyte maturation factor such as EGF, insulin, or FGF.

Primate primordial stem cells can also be used to generate cells that have characteristic markers of cardiomyocytes and spontaneous periodic contractile activity. Differentiation in this way is facilitated by nucleotide analogs that affect DNA methylation (such as 5-aza-deoxy-cytidine), growth factors, and bone morphogenic proteins. The cells can be further enriched by density-based cell separation, and maintained in media containing creatine, carnitine, and taurine.

Additionally, stem cells such as primate primordial stem cells can be directed to differentiate into mesenchymal cells in a medium containing a bone morphogenic protein (BMP), a ligand for the human TGF-.beta. receptor, or a ligand for the human vitamin D receptor. The medium may further comprise dexamethasone, ascorbic acid-2-phosphate, and sources of calcium and phosphate. In preferred embodiments, derivative cells have phenotypic features of cells of the osteoblast lineage.

Differentiated cells derived from stem cells such as primate primordial stem cells can be also be used for tissue reconstitution or regeneration in a human patient in need thereof. The cells are administered in a manner that permits them to graft to the intended tissue site and reconstitute or regenerate the functionally deficient area. For instance, neural precursor cells can be transplanted directly into parenchymal or intrathecal sites of the central nervous system, according to the disease being treated. The efficacy of neural cell transplants can be assessed in a rat model for acutely injured spinal cord, as described by McDonald et al. ((1999) Nat. Med. 5:1410, 1999; and Kim et al. Nature, 418:50, 2002). Successful transplants will show transplant-derived cells present in the lesion 2-5 weeks later, differentiated into astrocytes, oligodendrocytes, and/or neurons, and migrating along the spinal cord from the lesioned end, and an improvement in gait, coordination, and weight-bearing.

Similarly, the efficacy of cardiomyocytes can be assessed in a suitable animal model of cardiac injury or dysfunction, e.g., an animal model for cardiac cryoinjury where about 55% of the left ventricular wall tissue becomes scar tissue without treatment (Li, et al. (1996), Ann. Thorac. Surg., vol. 62:654; Sakai, et al. (1999), Ann. Thorac. Surg., vol. 8:2074; Sakai, et al. (1999), J. Thorac. Cardiovasc. Surg., vol. 118:715). Successful treatment will reduce the area of the scar, limit scar expansion, and improve heart function as determined by systolic, diastolic, and developed pressure (Kehat, et al. (2004)). Cardiac injury can also be modeled, for example, using an embolization coil in the distal portion of the left anterior descending artery (Watanabe, et al. (1998), Cell Transplant., vol. 7:239), or by ligation of the left anterior descending coronary artery (Min, et al. (2002), J. Appl. Physiol., vol. 92:288). Efficacy of treatment can be evaluated by histology and cardiac function. Cardiomyocyte preparations embodied in this invention can be used in therapy to regenerate cardiac muscle and treat insufficient cardiac function.

Liver function can also be restored by administering hepatocytes and hepatocyte precursors differentiated from, for example, primate pluripotent stem cells grown in accordance with this invention. These differentiated cells can be assessed in animal models for ability to repair liver damage. One such example is damage caused by intraperitoneal injection of D-galactosamine (Dabeva et al., Am. J. Pathol. 143:1606, 1993). Treatment efficacy can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself, for example, following fulminant hepatic failure.

Genetically Modified Primate Stem Cells

The methods of the present invention may also be used in association with stem cells, e.g., primate stem cell lines, having one or more genetic modifications. As is apparent to one of ordinary skill in the art, altered expression of gene products can be achieved by modifying the coding sequence of a gene product or by altering flanking regions of the coding sequence. Thus, as used herein, the terms "genetic modification" and the like include alterations to the sequence encoding a gene product, as well as alterations to flanking regions, in particular to the 5' upstream region of the coding sequence (including the promoter). Similarly, the term "gene" encompasses all or part of the coding sequence and the regulatory sequences that may be present flanking the coding sequence, as well as other sequences flanking the coding sequence. Genetic modifications may be permanent or transient. Preferred permanent modifications are those that do not adversely affect chromosome stability or cell replication. Such modifications are preferably introduced by recombination or otherwise by insertion into a chromosome (as may be mediated, for example, by an engineered retroviral vector). Transient modifications are generally obtained by introducing an extrachromosomal genetic element into a cell by any suitable technique. Regardless of the permanence of a particular genetic modification, in embodiments wherein one or more genes are introduced, their expression may be inducible or constitutive. The design, content, stability, etc. of a particular genetic construct made for use in practicing the invention is left to the discretion of the artisan, as these will vary depending on the intended result.

After introducing a desired genetic modification, a particularly effective way of enriching genetically modified cells is positive selection using resistance to a drug such as neomycin. To accomplish this, the cells can be genetically altered by contacting them simultaneously with a vector system harboring the gene(s) of interest and a vector system that provides the drug resistance gene. Alternatively, the drug resistance gene can be built into the same vector as the gene(s) of interest. After transfection has taken place, the cultures are treated with the corresponding drug, and untransfected cells are eliminated.

One or more genes or nucleic acid molecules are introduced into, or one or more genes are modified in, these stem cells, and the cells are grown in culture, to produce a clone population having the desired genetic modifications. Depending upon the genetic modification(s) made, the cells may continue to be propagated in a substantially undifferentiated state in accordance with the invention. Alternatively, they may be allowed (or induced) to differentiate. Primate-derived primordial stem cells having such genetic modifications have important applications, especially with respect to applications where euploid primate cells having genetic modifications are useful or required. Examples of such applications include, but are not limited to, the development of cell-based models for primate, especially human, diseases, as well as the development of specialized tissues for transplantation. Genetically modified stem cells cultured in accordance with the invention, including primate primordial stem cells, especially human embryonic stem cells, also have many other therapeutic applications, including in gene therapy (e.g., to compensate for a single gene defect), and as tissue for grafting or implantation, and to treat other diseases and disorders. Examples of diseases caused by single gene defects include myotonic dystrophy, cystic fibrosis, sickle cell anemia, Tay Sachs disease, and hemophilia.

For therapeutic application, cells prepared according to this invention (be they totipotent or pluripotent cells or differentiated cells derived therefrom) are typically supplied in the form of a pharmaceutical composition comprising an isotonic excipient, and are prepared under conditions that are sufficiently sterile for human administration. For general principles in medicinal formulation of cell compositions, see "Cell Therapy: Stem Cell Transplantation, Gene Therapy, and Cellular Immunotherapy," by Morstyn & Sheridan eds, Cambridge University Press, 1996; and "Hematopoietic Stem Cell Therapy," E. D. Ball, J. Lister & P. Law, Churchill Livingstone, 2000. The cells may be packaged in a device or container suitable for distribution or clinical use, optionally accompanied by information relating to use of the cells in tissue regeneration or for restoring a therapeutically important metabolic function.

General methods in molecular genetics and genetic engineering are described in the current editions of "Molecular Cloning: A Laboratory Manual" (Sambrook, et al., Cold Spring Harbor); Gene Transfer Vectors for Mammalian Cells (Miller & Calos eds.); and "Current Protocols in Molecular Biology" (Ausubel, et al. eds., Wiley & Sons). Cell biology, protein chemistry, and antibody techniques can be found in "Current Protocols in Protein Science" (Colligan, et al. eds., Wiley & Sons); "Current Protocols in Cell Biology" (Bonifacino, et al., Wiley & Sons) and "Current Protocols in Immunology" (Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

The present invention will be further described by the following nonlimiting example.

EXAMPLE 1

Human Embryonic Stem cells (hESCs) are pluripotent cells derived from the inner cell mass of human embryos at the preimplantation stage that are capable of in vitro differentiation into virtually every cell type found in the adult body (Thomson et al., Science 282:1145-1147, 1998). hESCs hold great promise for cell-based therapies and drug screening applications. However, growing and processing large quantities of undifferentiated hESCs is a challenging task.

Conventionally, hESCs are passaged as clusters, which can limit their growth efficiency and use in downstream applications. Initially, hESCs were isolated and passaged by mechanical dissociation (Thomson et al., Science 282:1145-1147, 1998). Since the development of this technique, several variations for the derivation and maintenance of hESC were reported (Amit et al., Biol. Reprod. 70:837-845, 2004; Klimanskaya et al., Lancet 365, 1636-1641, 2005; Stojkovic et al., Stem Cells 23:306-314, 2005; Xu et al., Nat. Biotechnol. 19:971-974, 2001; Xu et al., Nat. Methods 2:185-190, 2005). However, most approaches require close human supervision of the quality of hESC colonies. To maintain the high quality of hESC cultures, colonies having a healthy, undifferentiated morphology are visually identified, manually selected, and passaged as clusters (alternatively, colonies having poor differentiated morphologies are removed from culture). Recently, an automated method for mechanical hESC passaging was proposed (Joannides et al., Stem Cells 24:230-235, 2006). However, this approach requires specialized, custom-produced equipment and the ability of this system to maintain the pluripotency of hESC cultures over many passages has not been documented.

Passaging of hESCs as clusters imposes major limitations for downstream applications requiring single cell preparations, such as cell separation by flow cytometry (FACS) or the dispensing of live hESCs into multiwell plates for use in high throughput screening. However, in contrast to murine ESCs, which can be efficiently passaged by dissociation into single cells, the dissociation of hESCs into single cells limits their ability to survive and expand as pluripotent cultures likely resulting from physical damage (Amit et al., Dev. Biol. 227: 271-278, 2000). Recently, the derivation of 17 lines that can be propagated using trypsin dissociation has been described (Cowan et al., New Engl. J. Med. 350:1353-1356, 2004), but these hESCs also propagated as small clusters rather than single cells. Dissociation of hESCs to single cells with trypsin results in a dramatic decrease in plating efficiency (less than 3%) during the first 5-10 passages and the emerging sub-lines that arise invariably acquire detectable karyotypic abnormalities after 30 passages (Hasegawa et al., Stem Cells 24:2649-2660, 2006).

We applied Accutase (a commercially available cell detachment solution) for single cell propagation of pluripotent hESCs. Contrary to trypsin dissociation, Accutase treatment does not significantly affect the plating efficiency of hESC dissociation into single cells. Using an hESC line engineered with an Oct4-eGFP reporter construct demonstrates that cultures dissociated with Accutase to single cells at each passage maintain a higher proportion of Oct4/eGFP-positive cells as compared to collagenase-passaged hESCs. Accutase-treated hESCs can be grown to a high density as monolayers, and yet retain their pluripotency. The single cell dissociation with Accutase does not require human supervision for selection of colonies with undifferentiated morphologies and thus could be easily adopted by any laboratory currently using regular cell culture techniques.

Methods hESC Culturing.

hESCs were cultured on growth factor-reduced Matrigel coated plates (Becton Dickinson) and inactivated (irradiated) MEFs (Specialty Media) in Knockout DMEM (GIBCO), 20% Knockout serum replacement (GIBCO), 10 mM nonessential amino acids (GIBCO), 200 mM L-glutamine (GIBCO), 55 mM 2-mercaptoethanol (Gibco), penicillin/streptomycin (GIBCO), and 25 µg/L recombinant human basic Fibroblast Growth Factor (Sigma). The medium was changed daily.

Passaging of hESCs with Collagenase.

Human ESCs were treated using 1 mg/mL collagenase IV solution (Gibco, dissolved in Knockout DMEM) and incubated for approximately 5 minutes until the edges of colonies began to curl. The collagenase IV solution was removed and the colonies washed with dPBS twice. The differentiated cells were removed mechanically with micro pipette tips and then undifferentiated colonies were cut into small pieces and detached from the plastic by trituration. The hESC clusters were transferred to a new plate containing standard hESC medium (see above).

Single Cell Passaging of hESCs with Accutase.

Human ESCs were washed twice with $Ca^{2+}$- and $Mg^{2+}$-free PBS and treated with Accutase™ (Chemicon) in a 37 O incubator for ~5-10 minutes to dissociate the colonies into single cells. After gentle tritutation the cells were collected by centrifugation (800 rpm for 5 minutes) and replated at ~$1 \times 10^5$ cells/ml ($5 \times 10^5$ cells per well of a 6 well plate) using standard hESC culturing conditions. Cells were passaged between day 5 and 10, depending on the initial plating density and the experimental setup. The cultures were washed with PBS every time before changing medium as soon they reached 70% confluency.

FACS Analysis and Single Cell Sorting.

Both the Accutase- and the collagenase-treated hESCs engineered with the Oct4-eGFP reporter were dissociated to single cells using Accutase. Single cells were collected by centrifugation and washed twice with PBS. Seven-aminoactinomcin D (7-AAD, Molecular Probe) was added to each sample according to manufacturer instructions. The cells were sorted into eGFP+ and eGFP-fractions using FACS Vantage-Diva (BD Bioscience) and plated in standard hESC culturing conditions. Single hESCs were analyzed using a FACSCanto instrument (BD Bioscience).

Immunofluoresence Assay/Antibody Staining.

hESC colonies were fixed with 4% paraformaldehyde for 5 minutes at room temperature and washed with $Ca^{2+}$- and $Mg^{2+}$-free PBS. The fixed cells were stained overnight at 4° C. using primary antibodies specific for Oct4, SSEA4, Nanog, Sox2, Nestin, MF20, FLK-1, PDGFRα, AFP, and CD15 followed by incubation with an appropriate secondary fluorescent-conjugated antobdies. All primary antibodies are from Chemicon, except Oct4 and SSEA4 specific antibodies (Santa Cruz). Secondary, FITC/Rho conjugated antibodies were from Jackson Laboratories and 488/Cy5 conjugated antibodies were obtained from Molecular Probes.

Results

Single Cell Accutase Dissociation of hESCs does not Decrease Plating Efficiency.

Treatment of hESC (H9) colonies with Accutase resulted in the complete dissociation of each colony to single cells in suspension over 5-10 minutes. In contrast to collagenase, which digests the extracellular matrix, Accutase digests cell surface proteins that mediate contacts between cells as well as cell-matrix contacts. Thus, Accutase treatment allows the efficient dissociation of cells both in the middle of the hES cell colony and those cells on the periphery. Cells with differentiated morphologies (e.g. feeder Mouse Embryonic Fibroblasts (MEFs)) require less time to detach from the plastic, allowing efficient cleaning of cultures with intermediate PBS washes. After the gentle trituration, hESCs can be easily dispersed into small clusters and additional incubation with Accutase followed by gently trituration results in single cell suspensions.

Figure 1:
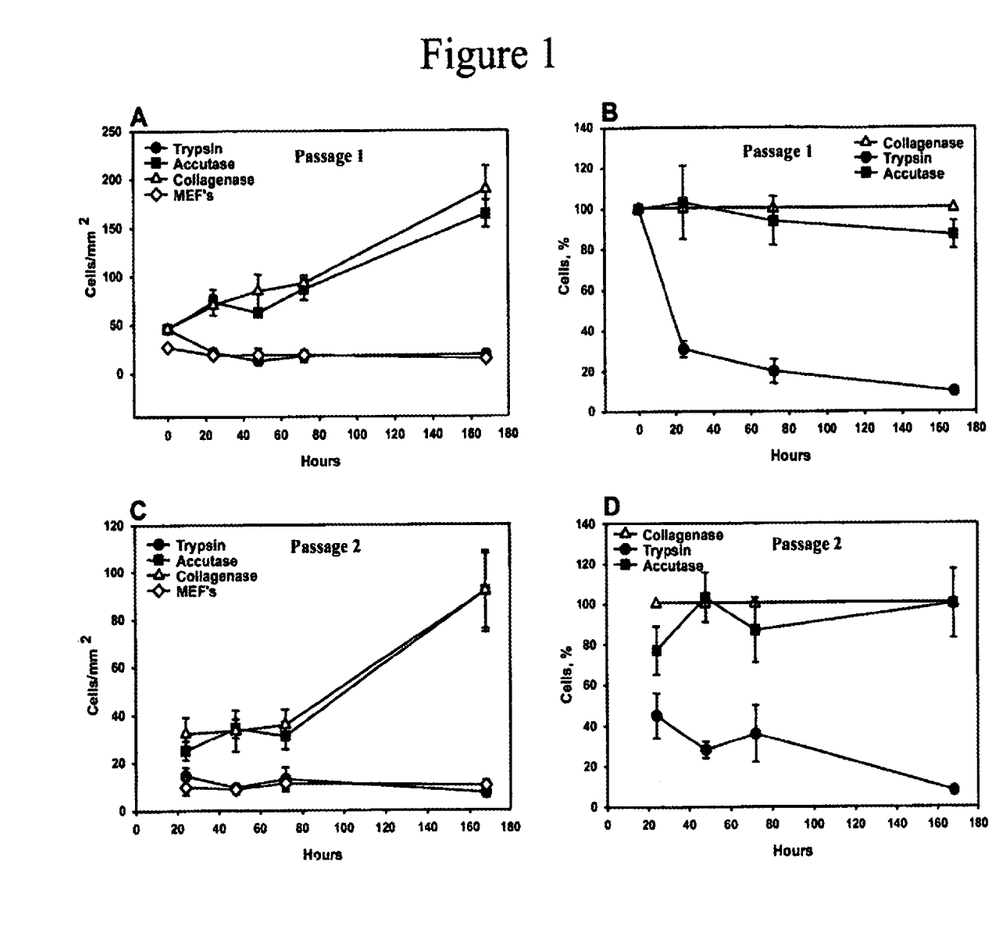
FIG. 1 shows that Accutase dissociation of hESCs to single cells maintains the proliferation rate of hESCs. Standard cultures of hESCs (passaged with collagenase) were split into three equal parts and propagated by dissociation to single cells with Accutase or trypsin (gentle dissociation with 0.05% trypsin). The collagenase-treated cultures were maintained in parallel. (A) Total number of cells in each culture over the first 7 days; (B) Percentage of hES cells growing in Accutase and trypsin cultures compared to collagenase cultures (always 100%) over the first 7 days. (C, D) similar plots to A and B for the second consecutive passage of hESCs. hESCs were grown on irradiated (mitotically inactive) MEF feeder cells equally present in each culture.

To determine if dissociation of hESCs to single cells with Accutase affects cell viability, the proliferation kinetics of collagenase-, Accutase- and trypsin-passaged hESCs were compared. In contrast to trypsin dissociation, Accutase-dissociated single hESCs maintained a high proliferation capacity from the first day in culture (FIG. 1A). In fact, no significant differences were observed between collagenase and Accutase-propagated hESCs (FIG. 1B). Similar kinetics was observed for the second consecutive passage (FIG. 1C, D). In contrast, trypsin-dissociated single hESCs failed to proliferate and form colonies, in agreement with the very low plating efficiency and proliferation rate reported earlier (Hasegawa et al., Stem Cells 24:2649-2660, 2006). In subsequent experiments, collagenase- and Accutase-treated cells also had similar proliferation kinetics. These results suggest that, in contrast to trypsin dissociation, the Accutase treatment does not result in massive cell death. The majority of hESCs present in the culture continue to proliferate and form numerous colonies. Several different hESC lines were propagated with Accutase for various numbers of passages; all retained their proliferation rate and undifferentiated morphology of hESC colonies, as well as the ability to terminally differentiate (Table 1). No significant differences occurred between various hESC lines in any of the above outcomes following Accutase treatment. The focus of this study is on the H9 clone engineered with an Oct4-eGFP expression cassette and propagated with Accutase by dissociation to single cell for over 20 passages.

TABLE 1

Summary of hESC lines propagated with Accutase. The number of passages with Accutase is indicated in the last column. Various hESC lines were propagated between 16 and 98 passages when switched to Accutase treatment.

| hESC lines | Growth conditions | Previous passaging technique | Passaged with Accutase |
| --- | --- | --- | --- |
| H9 Oct4-eGFP | Matrigel + MEFs | Collagenase | P20 |
| H9 | Matrigel + MEFs | Collagenase | P10 |
| H9 | Gelatin + human feeders | Manual dissection | P3 |
| H1 | Matrigel + MEFs | Collagenase | P3 |
| H14 | Matrigel + MEFs | Collagenase | P3 |
| HES25 | Gelatin + MEFs | Manual dissection | P3 |
| HUES7 | Matrigel + MEFs | Trypsin | P3 |

Generation and Validation of hESCs Engineered with an Oct4-eGFP Cassette.

H9 cells engineered to express eGFP under the control of 4 Kb Oct-4 promoter, which is known to drive specific reporter expression in blastocyst and pluripotent ES cells (Fuhrmann et al., Cell. Molec. Biol. [Noisy-le-Grand, France] 45:717-724, 1999; Gerrard et al., Stem Cells 23:124-133, 2005; Ovitt and Scholer, Molec. Human Repro. 4:1021-1031, 1998; Scholer et al., EMBO J. 9:2185-2195, 1990; Yeom et al., Development 122:881-894, 1996), were used to monitor the propagation of pluripotent hESCs. To verify the fidelity of the Oct4-eGFP reporter, immunostaining with Oct4-specific antibodies was used to detect endogenous Oct4 protein levels as compared to eGFP reporter activity.

eGFP was expressed in all cells that were positive for endogenous Oct4 protein. A few cells weakly positive for eGFP and negative for endogenous Oct4 protein, were found scattered throughout the colony. Individual cell counts showed that weakly eGFP positive cells represented less than 0.1% of all eGFP-positive cells (i.e. 99.9% of eGFP-positive cells are also positive for the endogenous Oct4). The slow degradation of eGFP is likely to be responsible for these weakly eGFP-positive, Oct4-negative cells. Differentiated cells (e.g. day 6 embryoid body) entirely lack Oct4-eGFP fluorescence, demonstrating that the lentiviral Oct4-eGFP cassette faithfully labels pluripotent hESCs as positive for the endogenous Oct4 protein.

Accutase-Passaged hESCs Form Monolayers.

In order to gain insight into the formation and growth of colonies after Accutase-induced dissociation of hESCs, Oct4-eGFP hES cell colonies were monitored using bright field and fluorescent microscopy. As expected, Accutase-treated hESCs retained eGFP fluorescence after dissociation to single cells. No substantial decrease in plating efficiency of Accutase dissociated single hESCs was observed. Collagenase-passaged cells, propagated as small clusters, were monitored in parallel. Accutase-treated single hESCs attached to the plates after one day and started to grow as small colonies. Twice daily observations of individual growing colonies provided evidence that the majority of colonies grew from individual single cells and did not form via aggregation. Because the Accutase-treated cultures began as single (possibly few) cells, the hESC colonies were smaller in these cultures as compared to collagenase-treated cultures at similar time points. No excessive floating debris or dead cells were observed in these cultures. When compared to collagenase-passaged cultures, the single cell-initiated Accutase colonies grew in denser arrays of smaller colonies. Nine to ten days after Accutase treatment, the colonies began to fuse, eventually forming a monolayer culture. The edges of the fused colonies remained well-formed and maintained the morphology of undifferentiated hESCs. To confirm that the hESCs remained pluripotent in monolayer culture, we examined the eGFP fluorescence of Oct4-eGFP-H9 cells grown in monolayer. Fluorescence microscopy showed that all cells in the monolayer cultures remained as pluripotent, Oct4-positive hESCs. Cells within the monolayer had characteristic hESC morphology with clearly distinct nuclei and cytoplasm, and exhibited different phases of cell cycle. The formation of hESC monolayers depended on the plating density. When split at a 1:3 ratio, Accutase-dissociated hESCs routinely formed a monolayer around 11-12 days and could be propagated in this way for as many passages as necessary. No adverse effect of monolayer cultures on hESC viability or pluripotency was detected.

Passaging with Accutase Maintains a High Proportion of Pluripotent hESCs.

Figure 2:
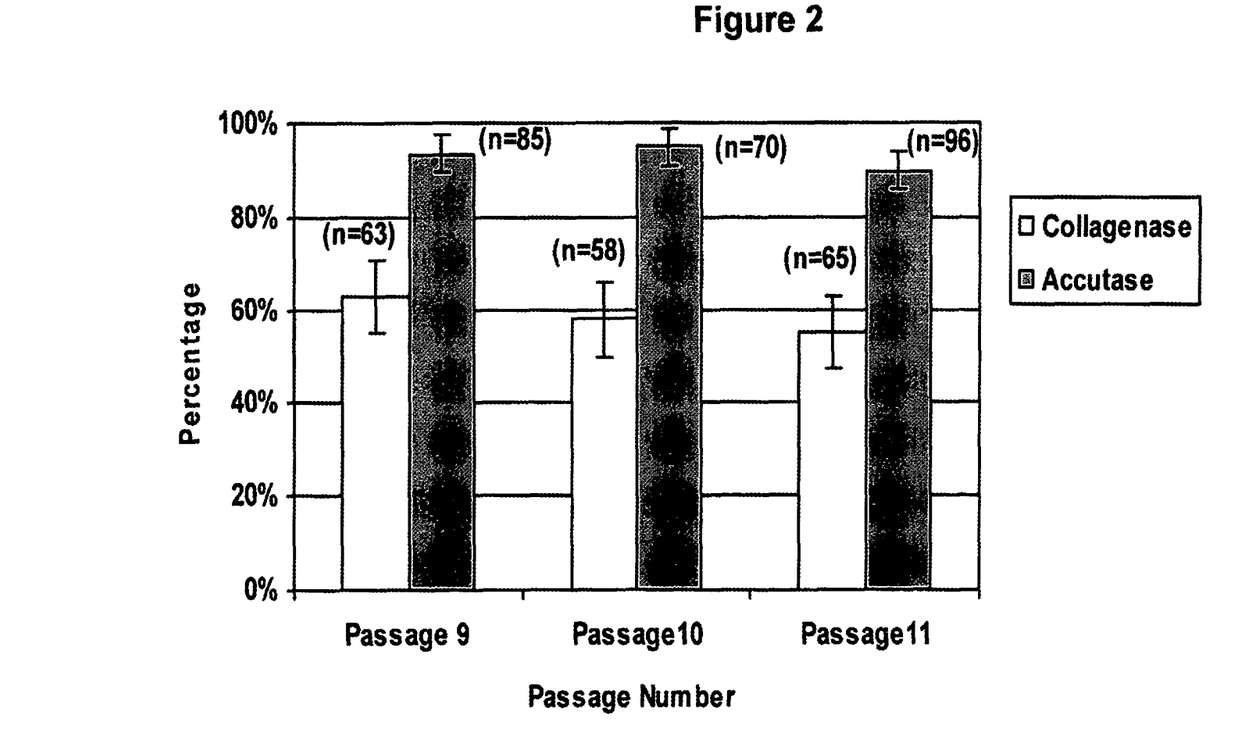
FIG. 2 shows that Accutase-passaged hESCs maintain high levels of undifferentiated cells. Comparable colonies from Accutase and collagenase treated cultures; most Accutase-passaged cultures show uniformly undifferentiated round colony morphology while collagenase-passaged cultures often show some differentiation. The numbers of undifferentiated colonies were counted in both Accutase- and collagenase-passaged hESCs using combined morphological and Oct4-eGFP criteria. The ratio of undifferentiated colonies to the total number of colonies in 7 microscopic fields was calculated for each culture at 9, 10, and 11 passages. Error bars represent standard deviation.
Figure 3:
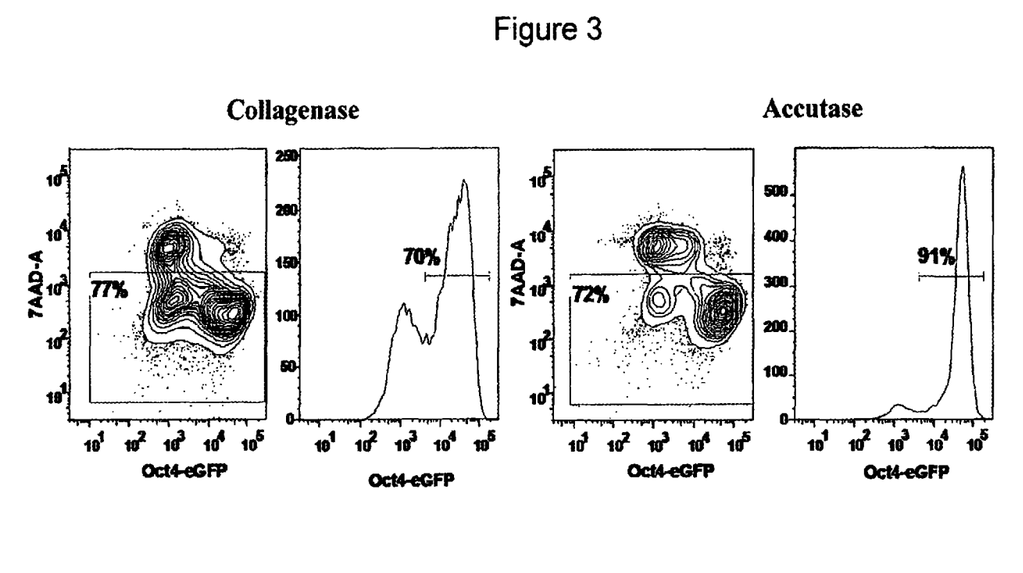
FIG. 3 shows representative FACS analysis (contour plots at 5% probability and histograms) of eGFP fluorescence of Accutase-passaged hESCs (Day 10) and collagenase-passaged hESCs (Day 7). The histogram profiles of 7AAD negative live cells (pink gates in contour plots) are shown along with the percentage of eGFP-positive cells (70% and 91% for collagenase and Accutase, respectively).

Colonies of Human ESCs passaged with Accutase maintained the characteristic undifferentiated morphology after 15 passages. Flow cytometry was used to quantify the amounts of undifferentiated cells within Oct4-eGFP H9 cultures propagated with collagenase and Accutase from passages 9 to 11. A higher percentage of eGFP-positive cells were observed in cultures passaged with Accutase (>90%) as compared to collagenase (~60%) (FIG. 2). In addition, Accutase-passaged Oct4-eGFP hESCs appeared more homogenous and showed a smaller percentage of cells displaying intermediate fluorescence levels (FIG. 3). To obtain an independent confirmation that hESCs propagated with Accutase remain undifferentiated, we used a H9 hESC line that was treated with Accutase for 10 passages. Immunostaining for the key markers of pluripotent hESCs:Oct4, SSEA4, Nanog and Sox2 revealed that a high proportion of cells within hESCs colonies were positive for these above markers. These data strongly suggest that hESC cultures passaged with Accutase maintained a higher proportion of undifferentiated cells. In addition, our comparative analysis indicates that Accutase-passaged hESC cultures maintained a higher proportion of undifferentiated (Oct4+) cells than collagenase-passaged cultures.

FACS Isolation and Propagation of Viable Single hESCs.

Figure 4:
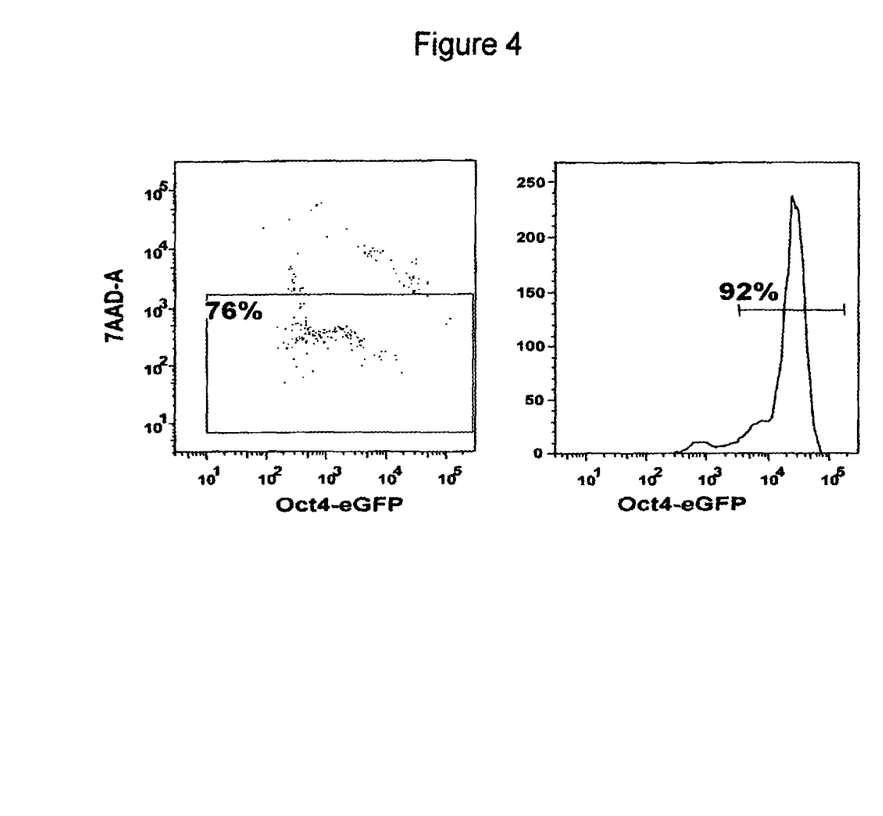
FIG. 4 shows representative FACS analysis of eGFP-positive sorted cells re-grown as colonies of pluripotent hESCs. Colonies of hESCs engineered with Oct4-eGFP were dissociated into single cells and sorted into eGFP-positive and eGFP-negative cells using FACS instrument. Sorted cells were plated in standard hESC conditions and sequential images of the colonies were captured using bright field and fluorescence microscopy. Representative FACS analysis of eGFP-positive sorted cells re-grown as colonies of pluripotent hESCs. The histogram profiles of 7AAD negative live cells (pink gates in contour plots at 5% probability) are shown along with the percentage of eGFP-positive cells (92%). The eGFP-negative cells failed to form viable colonies.

Prospective isolation of cells by flow cytometry is critical for numerous applications. However, by the definition of this technique, FACS procedure requires single cell preparations of viable cells. This single cell requirement is a major obstacle for the efficient application of flow cytometry techniques for separating hESCs. We investigated whether Accutase-dissociated single hESCs can be efficiently separated by flow cytometry. The Oct4-eGFP-hESC colonies were dissociated by Accutase and sorted into eGFP+ and eGFP− cells using a Vantage Diva FACS sorter. The single cells were deposited directly onto feeder layers of MEFs. FACS-isolated single hESCs quickly attached to the plate and grew as colonies with growth kinetics similar to that seen in Accutase-passaged hESCs that did not undergo FACS. For example, the small colonies started to fuse and form continuous monolayers around day 10-11. The eGFP-negative cells failed to form well-growing colonies. The monolayer cultures formed by FACS-isolated Oct4-eGFP hESCs were analyzed and found to have a similar fluorescence pattern with ~90% of cells falling within the narrow peak of eGFP-positive, undifferentiated hESCs (FIG. 4). The FACS-sorted hESCs were maintained for an additional five passages and behaved identically to the non-sorted hESCs passaged with Accutase. These results demonstrate that hESCs dissociated with Accutase to single cells can be isolated by flow cytometry as viable single cells and propagated as undifferentiated hESC cultures that are indistinguishable from the original cultures.

Differentiation of Accutase-Treated hESCs into Three Major Germ Layers.

Finally, we determined if human ES cells propagated with Accutase were capable of differentiation into the three major germ layers: ectoderm, mesoderm, and endoderm. The human ES cell line H9 and Oct4-EGFP H9 cells were maintained for 15-20 passages before assaying the differentiation into three germ layers. The differentiation into neuronal precursors was performed using a protocol recently described by Conti et al. (PLoS Biol. 3(9):e283, 2005). Under these conditions, Accutase-propagated cells efficiently differentiated into neuroectoderm, as monitored using a Nestin-specific antibody. The differentiation into the mesoderm and endoderm was performed using a classical embryo body formation protocol (Doetschman et al., J. Embryol. Exp. Morphol. 87:27-45, 1985). Mesodermal differentiation was monitored using markers for squamous epithelial and myelomonocytic lineages (CD15), muscle (MF20), and endothelium (FLK-1). The differentiation into the primitive endoderm/paraxial mesoderm was assessed using PDGF Ra, labeling during development first the primitive endoderm, then paraxial mesoderm, and finally many cell types in the embryonal mesenchyme (Takakura et al., J. Histochem. Cytochem. 45:883-893, 1997). Differentiation into the endoderm (likely the primitive endoderm) was also monitored using immunostaining against AFP. In summary, the staining revealed that the cells were positive for markers of all germ layers in differentiated hESC cultures propagated with Accutase. The efficiency of directed differentiation into neural precursors was similar to that of collagenase-treated hESCs.

Discussion

Here we describe a technique for hESC propagation with ACCUTASE® that allows the simple and routine dissociation of hESC colonies into single cells at each passage. ACCUTASE® is a mixture of enzymes with proteolytic, collagenolytic, and DNAse activities and is commercially available from several manufacturers (e.g. Innovative Cell Technologies, Chemicon/Millipore). The term "a mixture of enzymes with proteolytic, collagenolytic, and DNAse activities" has special meaning in this application such that it specifically refers only to ACCUTASE®. ACCUTASE® was used previously for passaging different cell types, for example neural precursor cells (Wachs et al., Lab. Invest. 83:949-962, 2003), and offered reduced cell death and improved culturing conditions.

Single cell dissociation of hESC colonies with Accutase resulted in continuous cultures of hESCs that were viable and highly pluripotent for at least 20 passages (the longest propagation time assayed in this work). Critically, no decrease in the proliferation rate after switching from collagenase to Accutase propagation of hESCs (i.e., from small clusters to single cells) was observed. This is in sharp contrast to conventional trypsin dissociation, which resulted in <3% plating efficiency and massive cell death during the initial 5-10 passages (Hasegawa et al., Stem Cells 24:2649-2660, 2006). The emerging hESC sub-lines with higher plating efficiency (up to 60%) that arose after trypsin treated inevitably acquired karyotypic changes after 30 passages (Hasegawa et al., Stem Cells 24:2649-2660, 2006). The dramatic cellular "crisis" period of 5-10 passages during the trypsin dissociation likely results from the selection of rare cells having karyotypic abnormalities that could confer a growth advantage. In contrast, Accutase-dissociated hESCs do not undergo this cellular crisis. In fact, we did not observe significant differences in the cell viability and cell proliferation kinetics between collagenase- and Accutase-passaged hESCs. These results alleviate the previous concerns regarding the selection and propagation of a subpopulation of genetically abnormal hESCs under the conditions of bulk culturing (Buzzard et al., Nat. Biotechnol. 22:381-382, 2004; Mitalipova et al., Nat. Biotechnol. 23:19-20, 2005). However, it is not clear whether karyotypic abnormalities or subtle genetic alterations (Maitra et al., Nat. Genet. 37:1099-1103, 2005) can be induced by the single cell culturing with Accutase, which would result in the slow accumulation of abnormal cells. Long-term cultures of Accutase-treated hESCs are currently being characterized to address this concern.

Accutase-passaged hESCs exhibit a higher proportion of undifferentiated hESCs as compared to collagenase-passaged cells. This is likely due to a faster detachment of differentiated cells from plastic that was observed in hESC cultures treated with Accutase. Ongoing experiments will determine the enzyme specificity in the Accutase mixture and their contribution to the dissociation of hESC colonies and differentiated cells.

Accutase-passaged hESCs can be grown at high density as monolayers, with viable single ES cells isolated by FACS to be further cultured as pluripotent hESCs. The ability to grow hESCs as monolayers allows a much higher cell density as compared to hESC growth in conventional clusters, which greatly increases the numbers of cells that can be recovered under the same culturing conditions. Passaging of hESCs with collagenase requires the periodic inspection of cultures to remove colonies with poor morphology indicative of the presence of differentiated cells. In contrast, all single hESCs after Accutase dissociation can be used for plating, thus allowing "unsupervised" hESC propagation. Indeed, the Accutase protocol does not require previous experience growing hESCs (e.g. selecting the hESCs colonies having healthy morphologies) and as such can be quickly adopted by any personnel who are well-versed in tissue culture techniques. Passaging with Accutase should allow a true automation of hESC growth, which will be indispensable for obtaining the large amounts of cells for clinical applications and high throughput drug screening. The latter application will especially benefit from deposition of precisely counted numbers of single cells into 96- or 384-well plates. Finally, dissociation to single cells will provide better control over the cellular environment for the purpose of directed differentiation and will improve gene delivery into hESCs (e.g. infection and transfection procedures).

REFERENCES

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition comprising:
a plurality of greater than 80 percent viable single human pluripotent embryonic stem cells in a bioreactor, comprising a mixture of enzymes with proteolytic, collagenolytic, and DNAse activities wherein the plurality of single embryonic stem cells maintains proliferative capacity from the first day in culture.

2. The composition of claim 1 wherein greater than 85 percent of said plurality of single human pluripotent embryonic stem cells are viable and pluripotent.

3. The composition of claim 1 wherein greater than 90 percent of said plurality of single human pluripotent embryonic stem cells are viable and pluripotent.

4. The composition of claim 1 wherein a substantially greater proportion of said plurality of single human pluripotent embryonic stem cells are undifferentiated than an otherwise similar population of single human pluripotent embryonic stem cells produced by collagenase digestion of a colony of pluripotent embryonic stem cells.

5. A composition comprising a plurality of greater than 75 percent viable single human pluripotent stem cells and a mixture of enzymes with proteolytic, collagenolytic, and DNAse activities in a bioreactor.

6. The composition of claim 5, wherein the plurality of single human pluripotent stem cells maintains proliferative capacity from the first day in culture and does not experience a decrease in plating efficiency wherein the bioreactor further comprises a matrix or feeder cells.

7. A composition comprising a plurality of greater than 75 percent viable single human pluripotent stem cells and a mixture of enzymes with proteolytic, collagenolytic, and DNAse activities, wherein the plurality of single human pluripotent stem cells maintains proliferative capacity from the first day in culture and does not experience a decrease in plating efficiency.

* * * * *

UNITED STATES PATENT AND TRADEMARK OFFICE
CERTIFICATE OF CORRECTION

| | |
|---|---|
| PATENT NO. | : 9,157,061 B2 |
| APPLICATION NO. | : 13/164639 |
| DATED | : October 13, 2015 |
| INVENTOR(S) | : Alexey Terskikh and Ruchi Bajpai |

It is certified that error appears in the above-identified patent and that said Letters Patent is hereby corrected as shown below:

In the Specification

In Column 1, Lines 17 through 20, please replace:
"The invention was supported, at least in part, by a grant from the Government of the United States of America (grant no. HD047313 from the National Institutes of Health). The Government may have certain rights to the invention."

With:
"This invention was made with government support under R21 HD047313 awarded by the National Institutes of Health. The government has certain rights in the invention."

Signed and Sealed this
Eighteenth Day of June, 2024

Katherine Kelly Vidal
*Director of the United States Patent and Trademark Office*